United States Patent [19]

Ponsford

[11] 4,153,714
[45] May 8, 1979

[54] 3-THIO-5-METHYL-7-OXO-1-AZABICYCLO[3,2,0]HEPT-2-ENE-2-CARBOXYLIC ACID ESTERS, THEIR PRODUCTION AND USE

[75] Inventor: Roger J. Ponsford, Horsham, England

[73] Assignee: Beecham Group Limited, United Kingdom

[21] Appl. No.: 891,710

[22] Filed: Mar. 30, 1978

[30] Foreign Application Priority Data

Apr. 1, 1977 [GB] United Kingdom ............... 13810/77

[51] Int. Cl.$^2$ .................... C07D 487/04; A61K 31/40
[52] U.S. Cl. ............................... 424/274; 260/239 A; 260/326.31
[58] Field of Search ..................... 260/326.31; 424/274

[56] References Cited

U.S. PATENT DOCUMENTS

| | | | |
|---|---|---|---|
| 3,950,357 | 4/1976 | Kahan et al. .................... | 260/326.31 |
| 4,011,216 | 3/1977 | Menard et al. .................. | 260/326.31 |

OTHER PUBLICATIONS

Bose et al., J. Org. Chem., vol. 39, pp. 115–116 (1974).

*Primary Examiner*—Donald G. Daus
*Attorney, Agent, or Firm*—Jacobs & Jacobs

[57] ABSTRACT

Antibacterial agents have been prepared of the formula (II):

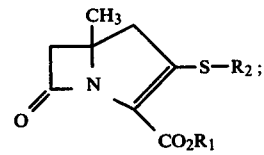

wherein $R_1$ is a group such that $CO_2R_1$ is an ester group and $R_2$ is a hydrocarbon of up to 7 carbon atoms optionally substituted by CN, $NO_2$, $OR_3$, $NH.CO.R_3$ or $CO_2R_3$ wherein $R_3$ is a lower alkyl.

13 Claims, No Drawings

3-THIO-5-METHYL-7-OXO-1-AZABICYCLO[3,2,0-]HEPT-2-ENE-2-CARBOXYLIC ACID ESTERS, THEIR PRODUCTION AND USE

The present invention relates to β-lactam antibacterials, to the process for their preparation and to compositions containing them.

British Pat. No. 1467413 discloses that the compound of the formula (I):

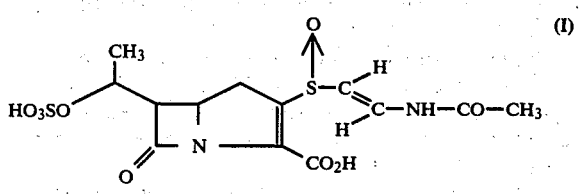

and its salts may be obtained by fermentation of strains of *Streptomyces olivaceus*. We have now found that a distinct class of synthetic antibacterial agents which contain a β-lactam ring fused to a pyrrolidine ring may be prepared.

Accordingly the present invention provides the compounds of the formula (II):

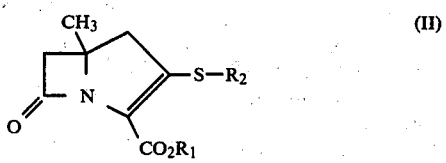

wherein $R_1$ is a group such that $CO_2R_1$ is an ester group and $R_2$ is a hydrocarbon group of up to 7 carbon atoms optionally substituted by a CN, $NO_2$, $OR_3$, $NH.CO.R_3$ or $CO_2R_3$ group where $R_3$ is a lower alkyl group.

When used herein the term "lower" means that the group contains 1-4 carbon atoms.

Suitably groups $R_1$ include alkyl groups of up to 12 carbon atoms, alkenyl groups of up to 12 carbon atoms, alkynyl groups of up to 12 carbon atoms, phenyl or benzyl groups or any of the aforesaid inertly substituted by lower alkoxyl, lower acyloxyl, halogen, nitro or the like group. Used herein "inertly substituted" means that the resulting group is stable and will not undergo rapid decomposition.

Favourably such groups contain a total of up to 8 carbon atoms.

Particularly suitable groups $R_1$ include lower alkyl groups optionally substituted by lower alkoxyl group; the benzyl group optionally substituted by lower alkoxyl, nitro, chloro or the like and those groups which are known to give rise to rapid in-vivo hydrolysis in penicillin esters.

Certain preferred groups $R_1$ include the methyl, methoxymethyl, benzyl methoxybenzyl, acetoxymethyl, pivaloyloxymethyl, α-ethoxycarbonyloxyethyl, phthalidyl, phthalimidomethyl and phenacyl groups.

Suitably $R_2$ is an optionally substituted alkyl, benzyl or phenyl group. Suitably $R_2$ is an optionally substituted alkenyl group.

Suitable groups $R_2$ include the methyl, ethyl, n-propyl, n-butyl, benzyl, 2-acetylaminoethyl, phenyl, p-nitrophenyl, cyanomethyl, methoxycarbonylmethyl, ethoxycarbonylmethyl and like groups. A further suitable group $R_2$ is the 2-acetylaminoethenyl group.

The compounds of the formula (II) most suitably have the configuration shown in formula (III):

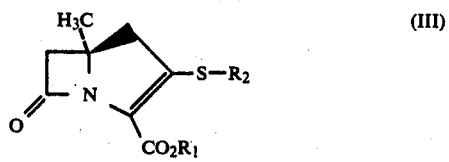

Thus the compounds of the invention are preferably those having the S-configuration at C-5. However, mixtures of the compounds of the formula (III) with their enantiomers, for example the 5RS compounds, are also included within this invention.

A reaction sequence leading to the compounds of this invention is as follows:

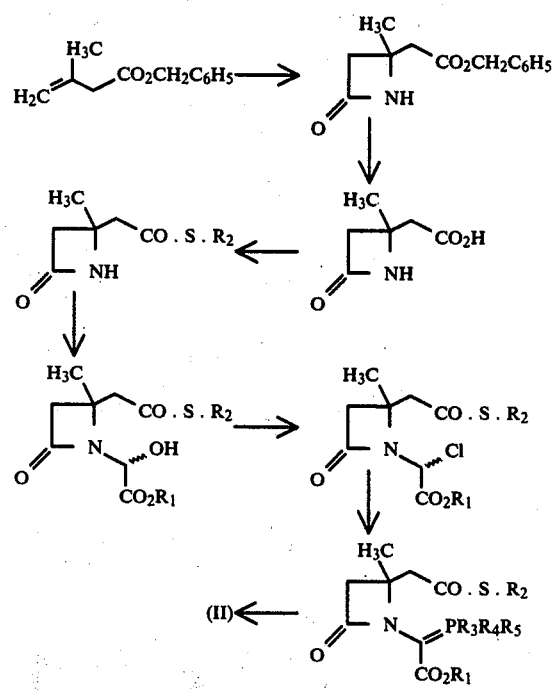

The process provided by this invention for the preparation of the compounds of the formula (II) comprises the ring closing elimination of the elements of $O=PR_3R_4R_5$ from a compound of the formula (IV):

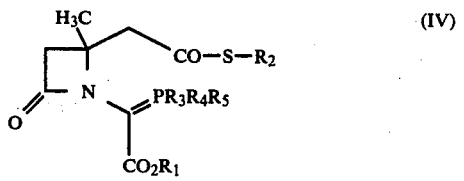

wherein $R_1$ and $R_2$ are as defined in relation to formula (II) and $R_3$, $R_4$ and $R_5$ are each lower alkyl, phenyl, methoxyphenyl or diloweralkylamino groups.

Most suitably $R_3$, $R_4$ and $R_5$ are each phenyl groups.

The ring closure is normally brought about by heating the compound of the formula (IV) in an inert solvent; for example temperatures of 90°–120° C. and more suitably 100°–110° C. may be employed in a solvent such as toluene or the like. The reaction is best carried out under dry conditions under an inert gas.

The compound of the formula (IV) may be prepared by the reaction of a corresponding compound of the formula (V):

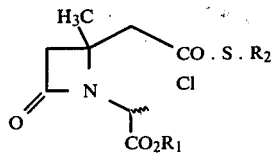

with a corresponding phosphine of the formula $PR_3R_4R_5$.

This reaction is normally effected in the presence of one equivalent of a base of relatively low nucleophilicity such as 2,6-lutidine at an ambient temperature in a dry solvent such as dioxan, tetrahydrofuran or the like.

The compound of the formula (V) may be prepared from the corresponding carbinol of the formula (VI):

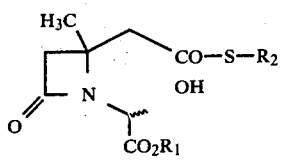

by reaction with thionyl chloride.

This reaction is also normally effected in the presence of one equivalent of a base of relatively low nucleophilicity in a dry solvent such as dioxane or tetrahydrofuran but in this instance the reaction is performed at a depressed temperature, for example $-30°$ to $-10°$ C.

The preceding carbinol may be prepared by the reaction of a compound of the formula (VII):

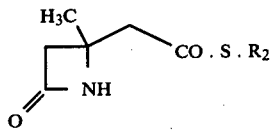

wherein $R_2$ is as defined in relation to formula (II) with a glyoxylic acid ester of the the formula (VIII):

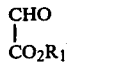

wherein $R_1$ is as defined in relation to formula (II).

Normally this reaction is carried out in an inert solvent at an elevated temperature, for example in dry benzene under reflux.

The thio-ester of the formula (VII) may be prepared by the esterification of an acid of the formula (IX):

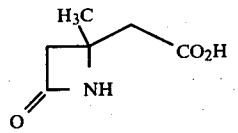

with a thiol of the formula $H.S.R_2$.

Any mild method of esterification may be employed but a particularly suitable method comprises the reaction of an acid of the formula (IX) with thionyl chloride or diethylphosphorochloridate and thereafter reacting with a thiol or its sodium or thalium salt. It is frequently convenient to carry out this reaction in the presence of a base of relatively low nucleophilicity such as pyridine, 2,6-lutidine or in the presence of triethylamine.

The compound of the formula (IX) may be prepared by the hydrogenation of its benzyl or like ester, for example using an approximately atmospheric pressure of hydrogen in the presence of catalyst such as palladium on charcoal.

The benzyl and like esters of the compound of the formula (IX) may be prepared by the reaction of chlorosulphonylisocyanate and a corresponding ester of 3-methyl-3-butenoic acid as described in the Examples herein.

This invention provides the compounds of the formulae (IV), (V), (VI), (VII) and (IX) and the hydrogenolysable esters of (IX) as useful intermediates. The process for the preparation of these compounds also forms part of this invention.

The present invention also provides a pharmaceutical composition which comprises a compound of the formula (II) as hereinbefore defined and a pharmaceutically acceptable carrier.

Most suitably the composition will be in unit dosage form and will comprise 25–1000 mg and more usually 50–500 mg of a compound of the formula (II).

Preferably the compound of the formula (II) present in such compositions will be in-vivo hydrolysable to the parent acid or its salt.

The composition of this invention may beneficially also comprise a penicillin or cephalosporin. Certain particularly suitable penicillins for use in these compositions include amoxycillin trihydrate and sodium amoxycillin.

The composition may be formulated using conventional carriers, for example filters, binders, lubricants and the like.

The composition of this invention may be used to treat infections due to suseptible organisms, for example gram-positive bacteria such as *Staphylococcus aureces*. The compositions may be used to treat such infections in humans or domestic mammals; for example the composition may be used to treat mastitis in cattle. The compositions may be used once or more times daily, for example 2–4 times daily, so that the total daily dose is about 10–50 mg/kg.

The following examples illustrate this invention.

EXAMPLE 1 t-Butyl 3-ethylthio-5-methyl-7-oxo-1-azabicyclo[3,2,0]hept-2-ene-2-carboxylate

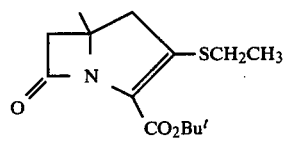

(i) Preparation of 4-methyl 4-benzyloxycarbonylmethylazetidin-2-one

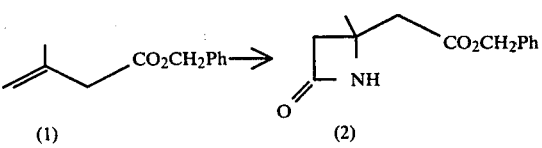

Benzyl 3-methyl 3-butenoate (1) (19 g) was dissolved in dry methylene chloride (20 ml) and treated with chlorosulphonylisocyanate (15 g; 10 ml) at room temperature. The reaction was stirred at room temperature for two days and the product hydrolysed by slow addition of the solution to sodium sulphite (15 g) in water (10 ml) below 25° with addition of 10% aqueous NaOH to maintain the pH between 4 and 6 (approximately 50 ml of NaOH solution required). The solution was partitioned and the aqueous phase extracted with ethyl acetate (3×50 ml). The organic phases were combined and dried over MgSO$_4$. Evaporation of the solvent and chromatography yielded the title compound (2; 30%). $v_{max}$ (CHCl$_3$) 3400, 1750 (br) cm$^{-1}$. δ ppm (CDCl$_3$) 1.48 (3H, s, CH$_3$), 2.74 (2H, s, CH$_2$CO$_2$CH$_2$Ph), 2.84 (2H, br. s., C3-methylene), 5.22 (2H, s, CO$_2$CH$_2$Ph), 6.99 (1H, br. s., NH [exchangeable]), 7.41 (5H, s, CO$_2$CH$_2$Ph). (Found: M 233.1057. C$_{13}$H$_{15}$NO$_3$ requires M 233.1057).

(ii) Preparation of 4-methyl-4-carboxymethylazetidin-2-one

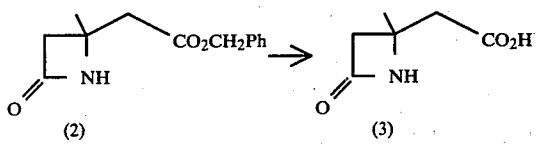

4-Methyl 4-benzyloxycarbonylmethyl azetidin-2-one (2) (2.3 g) was dissolved in ethanol (50 ml) and hydrogenated over 10% Pd/C (250 mg) for one hour. The solution was filtered and a further quantity of catalyst (250 mg) added. The hydrogenation was continued for a further hour and the solution filtered through kieselguhr and evaporated. 4-Methyl-4-carboxymethylazetidin-2-one (3) was obtained as a colourless gum which solidified on standing (1.4 g; 98%), $v_{max}$ (CHCl$_3$ or KBr disc) 3300, 1730, 1695 cm$^{-1}$. δ ppm (DMSO) 1.38 (3H, s, CH$_3$), 2.57 (2H, s, CH$_2$CO$_2$H), 2.57 and 2.81 (2H, two doublets [AB system] J 14 Hz C3-methylene), 7.90 (1H, s, NH [exchangeable]), 7.0 to 8.5 (1H, br. signal, CO$_2$H [exchangeable]).

(iii) Preparation of 4-methyl-4-ethylthiocarbonylmethylazetidin-2-one

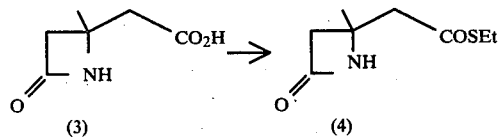

The acid (3) (1.4 g) was dissolved in dry chloroform (25 ml) and thionyl chloride (1.2 g) was added together with 2 drops of DMF to aid solution. The reaction was stirred at R.T. for two hours and ethyl mercaptan (0.72 g) was added followed by pyridine (1.82 g; 2 equivs.). The reaction was stirred at R.T. for a further hour, washed with 20% citric acid (2×15 ml) and 3% NaHCO$_3$ (3×15 ml), dried over MgSO$_4$ and the solvent evaporated to yield a viscous oil. Chromatography gave the title compound (4) as a light yellow oil (0.6 g; 32%), $v_{max}$ (CHCl$_3$) 3 400, 1760, 1680 cm$^{-1}$. δ ppm (CDCl$_3$) 1.22 (3H, t, J 7.5 Hz, SCH$_2$CH$_3$), 1.43 (3H, s, CH$_3$), 2.82 (6H, complex pattern SCH$_2$CH$_3$, CH$_2$COSEt and C3-methylene) (Found: M 187.0679. C$_8$H$_{13}$NO$_2$S requires M 187.0678).

(iv) Preparation of N-(1-hydroxy-1-butoxycarbonylmethyl)-4-methyl-4-ethylthiocarbonylmethylazetidin-2-one

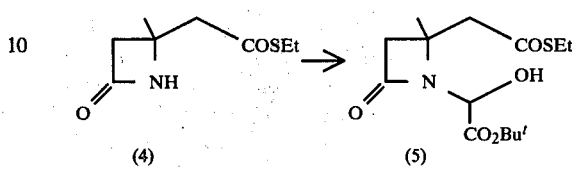

4-Methyl-4-ethylthiocarbonylmethylazetidin-2-one (4) (561 mg) was dissolved in dry benzene (10 ml) and added to a solution of t-butylglyoxylate (900 mg; 2 equivs.) in benzene (30 ml) which had previously been azeotroped for one hour. The solution was heated under reflux for six hours, the solvent evaporated and the product chromatographed. N-(1-Hydroxy-1-butoxycarbonylmethyl)-4-methyl-4-ethylthiocarbonylmethylazetidin-2-one (5) was collected as a light yellow oil (900 mg; 95%). $v_{max}$ (CHCl$_3$) 3500, 1760, 1740, 1680 cm$^{-1}$. δ ppm (CDCl$_3$) 1.31 (3H, t, J 7.5 Hz, SCH$_2$CH$_3$), 1.58 (9H, s, CO$_2$Bu$^t$), 1.61 (3H, s, CH$_3$), 3.00 (6H, complex pattern, CH$_2$'s), 4.50 (1H, br t, OH [exchangeable]), 5.07 and 5.35 (1H, two broad doublets which collapse to singlets on D$_2$O exchange, CHCO$_2$Bu$^t$ for two isomers).

(v) Preparation of 1-(1-t-butoxycarbonyl-1-triphenylphosphoranylidenemethyl)-4-methyl-4-ethylthiocarbonylmethylazetidin-2-one

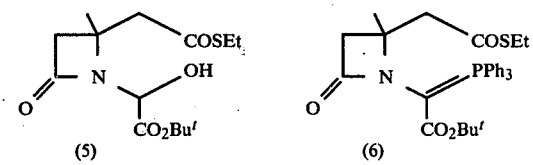

The carbinol (5) (634 mg) was dissolved in dry THF and cooled to −20°, 2,6-Lutidine (428 mg; 2 equivs.) and thionyl chloride (476 mg; 2 equivs.) in THF (5 ml) were added with stirring to the solution and stirring continued at −20° for a further twenty minutes. The mixture was filtered, the solvent removed under vacuum and the product dried by azeotroping twice with toluene. The residue was dissolved in dioxan (25 ml) and 2,6-lutidine (428 mg) added followed by triphenylphosphine (1.05 g; 2 equivs). After stirring at R.T. for three hours, the solvent was evaporated and the oil chromatographed to yield the title product (6) (650 mg) m.p. 178° $v_{max}$ (CHCl$_3$) 1735, 1680, 1640, 1600 cm$^{-1}$. δ ppm (CDCl$_3$) 0.9 (9H, s, CO$_2$Bu$^t$), 1.40 (3H, s, CH$_3$), 2.80 (6H, complex pattern CH$_2$'s), 7.50 (15H, br. m. (Ph)$_3$) (Found: C, 68.22; H, 6.61; N, 2.36; P, 5.06%. C$_{32}$H$_{36}$NO$_4$SP requires C, 68.45; H, 6.42; N, 2.50; P, 5.53%).

(vi) Preparation of t-butyl-3-ethylthio-5-methyl-7-oxo-1-azabicyclo[3,2,0]-hept-2-ene-2-carboxylate

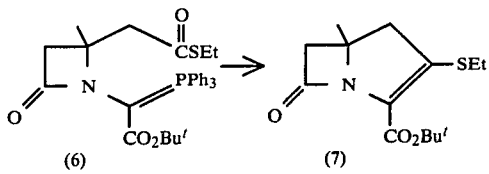

The phosphorane (6) (47 mg) was dissolved in dry toluene (3 ml) and heated under reflux and under argon for three days. The solvent was evaporated and the residue chromatographed to yield the title product (7) (7.5 mg; 32%) as a colourless oil. $\nu_{max}$ (CHCl$_3$) 1775, 1695 cm$^{-1}$. $\lambda_{max}$ (EtOH) 329 nm ($\epsilon$ 19,000). $\delta$ ppm (CDCl$_3$) 1.22 (3H, t, J 7.5 Hz, SCH$_2$CH$_3$), 1.44 (12H, s, CH$_3$ and CO$_2$Bu$^t$), 2.67 and 3.07 (2H, two doublets [AB q.] J 17 Hz, C6-H$_a$ and H$_b$), 2.69 (2H, q, J 7.5 Hz, SCH$_2$CH$_3$), 2.91 (2H, s, C4-methylene) (Found: M 283.1228. C$_{14}$H$_{21}$NO$_3$S requires M 283.1229).

EXAMPLE 2 t-Butyl-3-(2-acetamidoethyl)thio-5-methyl-7-oxo-1-azabicyclo[3,2,0]hept-2-ene-2-carboxylate

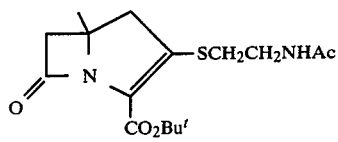

(i) Preparation of 4-methyl-4-(2-acetomidoethyl)thiocarboxymethylazetidin-2-one

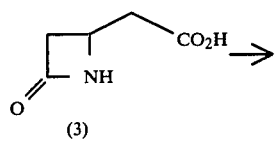

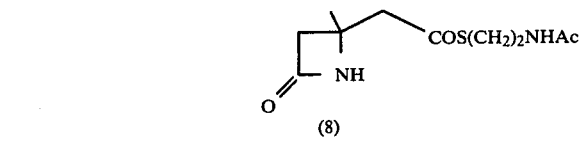

The acid (3) (286 mg) and triethylamine (222 mg) in dry THF (10 ml) were stirred at room temperature and to the solution was added a solution of diethyl phosphorochloridate (363 mg) in dry THF (5 ml) dropwise at RT under argon. The reaction was stirred at RT for three hours and filtered. To the filtrate was added Tl (1) acetamidoethylthiolate (710 mg) and the mixture stirred at RT overnight. The solvent was evaporated and the residue chromatographed to yield the thio ester (305 mg; 64%), $\nu_{max}$ (CHCl$_3$) 3,400, 1760, 1670 cm$^{-1}$. $\delta$ ppm (CDCl$_3$) 1.47 (3H, s, CH$_3$), 1.93 (3H, s, COCH$_3$) 2.80 and 2.91 (4H, two broad singlets, 3-CH$_2$ and CH$_2$CO), 2.98 (2H, t, J 6.5 Hz, SCH$_2$) 3.37 (2H, q, J 6.5 Hz, collapses to a triplet on D$_2$O exchange, CH$_2$NH), 6.22 (1H, br. s, NH [exchangeable]), 6.78 (1H, br. s. NH [exchangeable])

(ii) Preparation of N-(1-hydroxy-1-butoxycarbonylmethyl)-4-methyl-4-(2-acetamidoethyl)thiocarbonylmethylazetidin-2-one

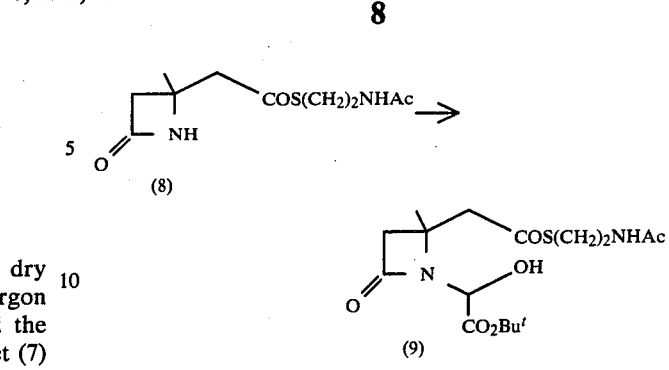

4-Methyl-4-(2-acetamidoethyl)thiocarboxymethylazetidin-2-one (9) (742 mg) was dissolved in dry benzene (10 ml) and was added to a solution of t-butylglyoxalate (900 mg) in benzene (30 ml) which had been previously azeotrobed for one hour. The solution was heated under reflux for six hours, the solvent evaporated and the residue chromatographed to yield the title product (600 mg; 71%) $\nu_{max}$ (CHCl$_3$) 3,500, 1765, 1680 cm$^{-1}$. $\delta$ ppm (CDCl$_3$) 1.47 (9H, s, OC(CH$_3$)$_3$), 1.54 (3H, s, CH$_3$) 1.93 (3H, s, COCH$_3$), 2.90 and 2.94 (2H, two AB quartets, 3-CH$_2$ for two isomers), 3.00 (4H, triplet superimposed on a broad singlet, J 6.5 Hz, SCH$_2$ and CH$_2$CO), 3.37 (2H, quartet collapsing to a triplet on D$_2$O exchange J 6.5 Hz, CH$_2$NHAc), 4.48 (1H, br.t. J 7 Hz, OH [exchangeable]), 4.83 and 5.23 (1H, two br. doublets, J 7 Hz, collapsing to singlets on D$_2$O exchange, CHOH for two isomers), 6.33 (1H, br.s., NH [exchangeable]).

(iii) Preparation of 1-(1-t-butoxycarbonyl-1-triphenylphosphoranylidenemethyl)-4-methyl-4-(2-acetamidoethyl)thiocarbonylmethylazetidin-2-one

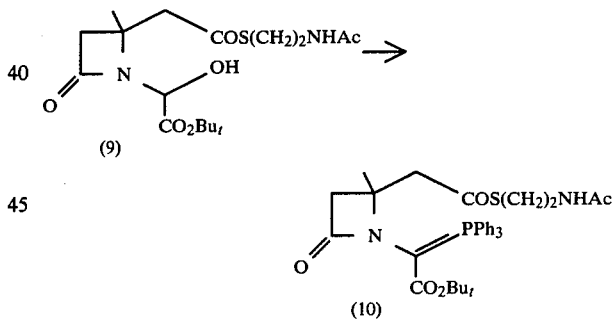

The carbinol (10) (562 mg) was dissolved in dry THF (15 ml) and cooled to −20°. 2,6 lutidine (321 mg) and thionyl chloride (714 mg) in THF (4 ml) were added in turn and stirring continued for 20 minutes. The mixture was filtered and dried by azeotroping twice with toluene. The residue was dissolved in dioxan (20 ml) and 2,6 lutidine (321 mg) was added slowly followed by triphenylphosphine (790 mg). After stirring overnight the solution was filtered, the solvent evaporated and the oil chromatographed to yield the phosphorane (520 mg; 56%) as a white solid from EtOAc/ether mp 189°-90°. $\nu_{max}$ (CHCl$_3$) 3,450, 1740, 1670, 1645 cm$^{-1}$ $\delta$ ppm (CDCl$_3$) 0.88 (9H, s, OC(CH$_3$)$_3$), 1.39 (3H, s, CH$_3$) 1.88 (3H, s, COCH$_3$), 2.92 and 3.30 (8H, two multiplets CH$_2$'s) 7.50 (15H, m, (Ph)$_3$). Found C, 66.03; H, 6.67; N, 4.61; S, 5.18; C$_{34}$H$_{39}$N$_2$O$_5$SP requires C, 66.02; H, 6.31; N, 4.53; S, 5.18.

(iv) Preparation of t-butyl 3-(2-acetamidoethyl)thio-5-methyl-7-oxo-1-azabicyclo[3,2,0]-hept-2-ene-2-carboxylate

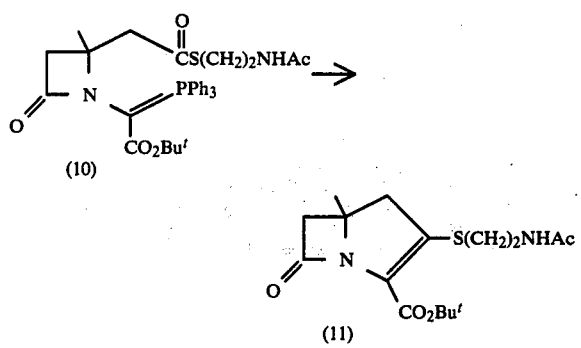

The phosphorane (45 mg) was refluxed in dry toluene (2 ml) under argon for three days. The solvent was evaporated and the product chromatographed using dioxan/ethyl acetate as eluent. The product only partially separated from the starting phosphorane. The crude product was stirred overnight with a solution of 40% aqueous formaldehyde (1 ml) in methylene chloride (2 ml) and the organic layer separated. The solvent was dried and evaporated to yield the product (4 mg) $\nu_{max}$ (CHCl$_3$) 3350, 1780, 1690, 1675 cm$^{-1}$.

EXAMPLE 3 t-Butyl-3-(2-methoxycarbonylmethyl)thio-5-methyl-7-oxo-1-azabicyclo[3,2,0]hept-2-ene-2-carboxylate

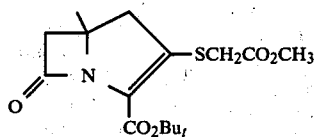

(i) Preparation of 4-methyl-4-(2-methoxycarbonylmethyl)thiocarboxymethylazetidin-2-one

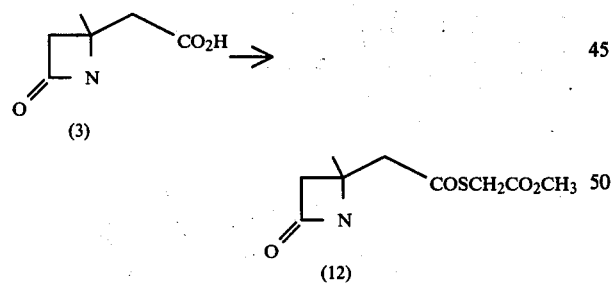

The acid (3) (1.29 g) and triethylamine (1.11 g) in dry T.H.F. (50 ml) were stirred at room temperature and a solution of diphenyl phosphinyl chloride in T.H.F. (20 ml) was added dropwise at R.T. under argon. The reaction was stirred at R.T. for half an hour and filtered. To the filtrate was added methylthioglycolate (2.2 g) and the reaction stirred at R.T. for an hour. The solvent was evaporated and the residual oil dissolved in ethyl acetate and washed with 3% bicarbonate solution (3×25 ml). The organic phase was dried and the solvent evaporated to yield an oil which after chromatography gave the thio ester (12) (500 mg; 22%) $\nu_{max}$ (CHCl$_3$) 1760 (br) 1695 cm$^{-1}$. δ ppm (CDCl$_3$) 1.48 (3H, s, CH$_3$) 2.70 and 2.89 (2H,[ABq.], J=17 Hz, 3-CH$_2$) 2.95 (2H, br.s., CH$_2$CO). 3.68 (3H, s, CO$_2$CH$_3$) 6.87 (1H, br.s. NH [exchangeable]).

(ii) Preparation of N-(1-hydroxy-1-butxoycarbonylmethyl)-4-methyl-4-(2-methoxycarbonylmethyl)thiocarbonylmethylazetidin-2-one

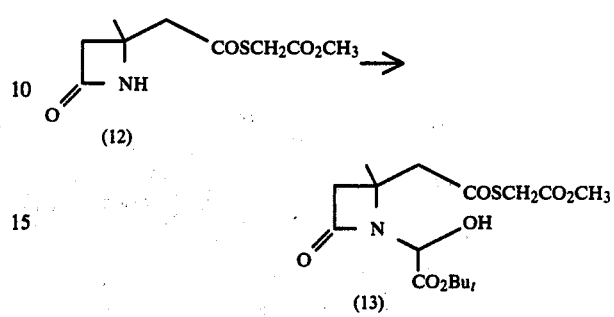

The thioester (12) (271 mg) was dissolved in dry benzene (10 ml) and a solution of t-butylglyoxalate (300 mg) in benzene (15 ml), which had been previously azeotroped to remove water, was refluxed for six hours. The solvent was evaporated to yield an oil which after chromatography gave the product (13) (320 mg; 89%) $\nu_{max}$ (CHCl$_3$) 1760, 1740, 1700 cm$^{-1}$. δ ppm (CDCl$_3$) 1.60 (12H, s, C(CH$_3$)$_3$ and CH$_3$) 3.12 and 3.32 (2H, [two superimposed AB quartets for two diastereoisomers] J=17 Hz, 3-CH$_2$) 3.23 (2H, br.s., CH$_2$CO) 3.83 (3H, s, CO$_2$CH$_3$) 4.53 (1H, br. m., OH [exchangeable]) 5.06 and 5.38 (two doublets, J=7 Hz, collapsing to two singlets after D$_2$O exchange, CH-OH, [two diastereoisomers]).

(iii) Preparation of 1-(1-t-butoxycarbonyl-1-triphenylphosphoranylidenemethyl)-4-methyl-4-(2-methoxycarbonylmethyl)thiocarbonylmethylazetidin-2-one

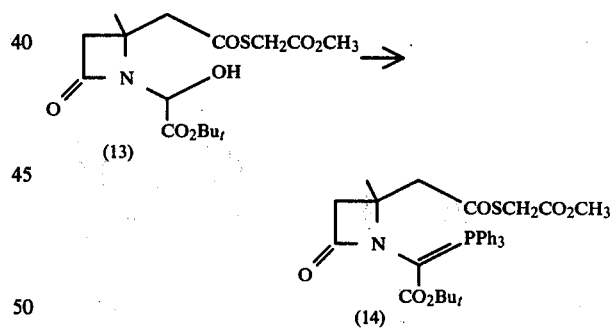

The carbinol (361 mg) was dissolved in dry T.H.F. (10 ml) at −20° and 2,6-lutidine (214 mg) and thionyl chloride (238 mg) in T.H.F. (5 ml) were added dropwise in turn. Stirring was continued at −20° for 20 mins. The solution was filtered and azeotroped twice with toluene. The residue was dissolved in dioxan (10 ml) and 2,6-lutidine (214 mg) was added followed by triphenylphosphine (500 mg). The solution was stirred at R.T. overnight filtered and the solvent removed under reduced pressure. The residue was chromatographed to yield the title product (250 mg; 41%) $\nu_{max}$ (CHCl$_3$) 1740, 1700, 1640, 1600 cm$^{-1}$.

(iv) Preparation of t-butyl 3-(2-methoxycarbonylmethyl)thio-5-methyl-7-oxo-1-azabicyclo[3,2,0]hept-2-ene-2-carboxylate

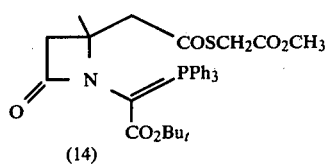
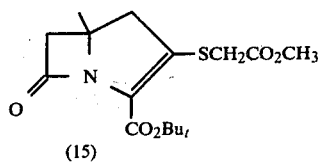

The phosphorane (100 mg) was refluxed in dry toluene (3 ml) under argon for 21 hours. The solvent was evaporated and the residue chromatographed to yield the product (15) (13 mg; 25%) $\nu_{max}$(CHCl$_3$) 1780, 1740, 1700, 1690 cm$^{-1}$. δ ppm (CDCl$_3$) 1.54 (12H, s, CO$_2$C(C$\underline{H}_3$)$_3$, and C$\underline{H}_3$) 3.87 and 3.19 (2H, [ABq.] J=17 Hz, C6-$\underline{H}$a and $\underline{H}$b) 3.02 (2H, br.s. C4-CH$_2$) 3.45 (2H, s, C$\underline{H}_2$CO$_2$CH$_3$) 3.72 (3H, s, CO$_2$C$\underline{H}_3$) Found: M 327.1130 C$_{15}$H$_{21}$NO$_5$S requires 327.1141.

EXAMPLE 4 t-Butyl-3-p-nitrophenylthio-5-methyl-7-oxo-1-azabicyclo[3,2,0]hept-2-ene-2-carboxylate

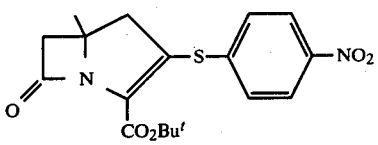

(i) Preparation of 4-methyl-4-p-nitrophenylthiocarbonylmethyl-azetidin-2-one

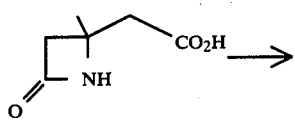

The acid (3) (1.29 g) was dissolved in dry CH$_2$Cl$_2$ (25 ml) and treated with SOCl$_2$ (1.2 g) followed by a few drops of DMF. After stirring at R.T. for two hours p-nitrothiophenol (1.55 g) was added, followed by pyridine (1.82 g) at −60°. The reaction was stirred at R.T. for three hours. It was then washed with 20% citric acid solution (2×25 ml), 3% NaHCO$_3$ (3×25 ml), dried over MgSO$_4$ and evaporated to yield an oil which was chromatographed on silica gel to yield the thioester (16) as an oil (500 mg; 18%). $\nu_{max}$(CHCl$_3$) 3400, 1760, 1710, 1525, 1340 cm$^{-1}$. δ ppm (CDCl$_3$) 1.54 (3H, s, C$\underline{H}_3$), 2.95 (2H, br s, C$\underline{H}_2$) 3.16 (2H, s, C$\underline{H}_2$), 7.07 (1H, br s, NH [exchangeable]), 7.72 and 8.38 (4H, ABq, J 9 Hz, aromatics) (Found: M 280.0504 C$_{12}$H$_{12}$N$_2$O$_4$S requires 280.0518).

(ii) Preparation of N-(1-hydroxy-1-butoxycarbonylmethyl)-4-methy-4-p-nitrohenylthiocarbonylmethyl-azetidin-2-one

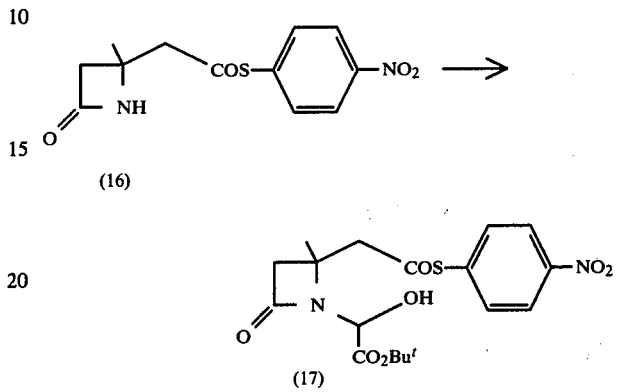

The thioester (16) (420 mg) was dissolved in dry benzene (15 ml) and added to a solution of t-butyl-glyoxylate (450 mg) in benzene (20 ml) which had been previously azeotroped for one hour. The solution was refluxed for six hours. The solvent was evaporated to yield an oil which after chromatography gave the product (300 mg; 49%). $\nu_{max}$ (CHCl$_3$) 1760, 1740, 1720 cm$^{-1}$. δ ppm (CDCl$_3$) 1.53 (9H, s, CO$_2$C(C$\underline{H}_3$)$_3$), 1.64 (3H, s, C$\underline{H}_3$), 2.80 to 3.40, complex pattern C$\underline{H}_2$'s), 4.38 (1H, br d, J 7.5 Hz, O$\underline{H}$ [exchangeable]), 4.97 and 5.34 (1H, two doublets collapsing to singlets after D$_2$O exchange, C$\underline{H}$OH for two diastereoisomers), 7.67 and 8.35 (4H, ABq, J 9 Hz, aromatic protons).

(iii) Preparation of 1-(1-t-butoxycarbonyl-1-triphenylphosphoranylidenemethyl)-4-methyl-4-p-nitrophenylthiocarbonylmethyl-azetidin-2-one

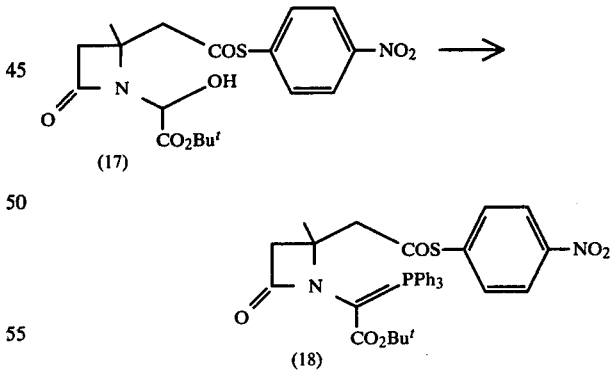

The carbinol (17) (205 mg) was dissolved in dry THF (10 ml) at −20° and 2,6 lutidine (107 mg) and thionyl chloride (119 mg) in THF (4 ml) were added dropwise. Stirring was continued at −20° for 20 min. The solution was filtered and azeotroped twice with toluene. The residue was dissolved in dioxan (15 ml) and 2,6 lutidine (107 mg) and triphenylphosphine (262 mg) were added. The mixture was stirred overnight at R.T. and filtered. Chromatography gave the product as an oil which crystallised from ether mp 125° (150 mg; 46%). $\nu_{max}$ (CHCl$_3$) 1740, 1640, 1605, 1525, 1345 cm$^{-1}$ (Found: C, 65.54; H, 5.71; N, 4.00; C$_{26}$H$_{35}$N$_2$O$_6$SP requires C, 66.06; H, 5.35; N, 4.28%).

(iv) Preparation of t-butyl-3-p-nitrophenylthio-5-methyl-7-oxo-1-azabicyclo-[3,2,0]-hept-2-ene-2-carboxylate

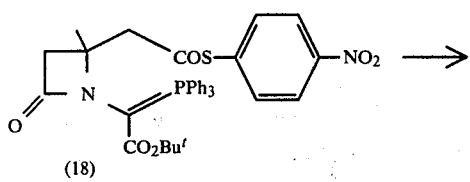
(18)

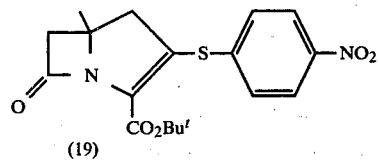
(19)

The phosphorane (32 mg) was dissolved in dry toluene (4 ml) and heated under reflux for five hours. The solvent was evaporated and the crude product chromatographed on silica gel to provide the product as an oil which crystallised from ether/petrol (bp. 60°–80°) mp 129°–131° (10 mg; 54%) $\nu_{max}$ (CHCl$_3$). 1785, 1710, 1690, 1525, 1345 cm$^{-1}$. δ ppm (CDCl$_3$) 1.47 (3H, s, CH$_3$), 1.56 (9H, s, C(CH$_3$)$_3$), 2.28 and 2.88 (2H, ABq, J 18 Hz, C6-Ha and Hb), 2.98 (2H, s, 4-CH$_2$), 7.57 and 8.15 (4H, ABq,q J 8 Hz, aromatics) λ$_{max}$ 265 (ε 10,000) 310 nm (ε12,200) (Found: M, 376.1094 C$_{18}$H$_{20}$N$_2$O$_5$S requires 376.1094).

EXAMPLE 5

Benzyl-3-p-nitrophenylthio-5-methyl-7-oxo-1-azabicyclo[3,2,0]-hept-2-ene-2-carboxylate

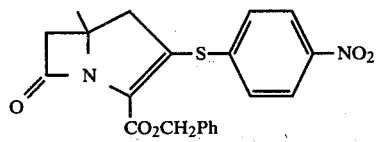

(i) Preparation of N-(1-hydroxy-1-benzyloxycarbonylmethyl)-4-methyl-4-p-nitrophenylthiocarbonylmethyl-azetidin-2-one

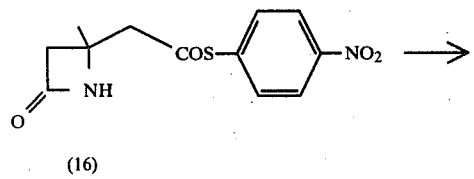
(16)

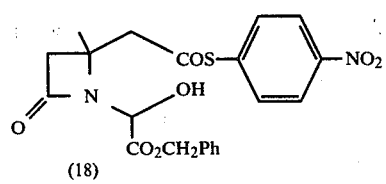
(18)

The thioester (16) (280 mg) was dissolved in dry benzene (10 ml) and added to a solution of benzylglyoxylate (500 mg) in benzene (20 ml) (previously azeotroped for one hour). The solution was refluxed for six hours, the solvent evaporated and the residue chromatographed to yield the product as an oil (200 mg; 45%). $\nu_{max}$ (CHCl$_3$) 1760 (br), 1720 cm$^{-1}$; δ ppm (CDCl$_3$) 1.52 and 1.70 (3H, two singlets, CH$_3$ [two diastereoisomers]), 2.70 to 3.50 (4H, complex pattern, CH$_2$'s), 4.48 (1H, br m, OH[exchangeable]), 5.35 (2H, s, CH$_2$), 5.30 and 5.59 (1H, two singlets, CHOH for two diastereoisomers which sharpens after D$_2$O exchange), 7.42 (5H, s, CH$_2$Ph), 7.93 and 7.98 (4H, two AB quartets, J 8 Hz, PhNO$_2$).

(ii) Preparation of 1-(1-benzyloxycarbonyl-1-triphenylphosphoranylidene methyl)-4-methyl-4-p-nitrophenylthiocarbonylmethyl-azetidin-2-one

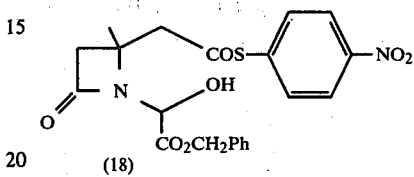
(18)

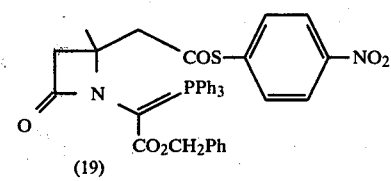
(19)

The thioester (167 mg) in dry THF was cooled to −20° and treated with 2,6-lutidine (81 mg) and thionyl chloride in THF (4 ml). Stirring was continued at −20° for 20 min. The mixture was filtered, azeotroped twice with toluene and the residue dissolved in dioxan (15 ml). 2,6-Lutidine (81 mg) and triphenylphosphine (196 mg) were added and the reaction was stirred overnight under argon and filtered. Evaporation of the solvent and chromatography yielded the product as an oil (146 mg; 56%). $\nu_{max}$ (CHCl$_3$) 1745, 1645, 1610 cm$^{-1}$.

(iii) Preparation of benzyl-3-p-nitrophenylthio-5-methyl-7-oxo-1-azabicyclo[3,2,0]hept-2-ene-2-carboxylate

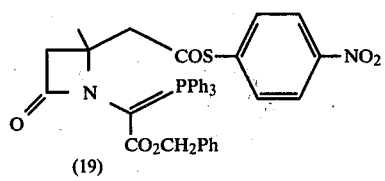
(19)

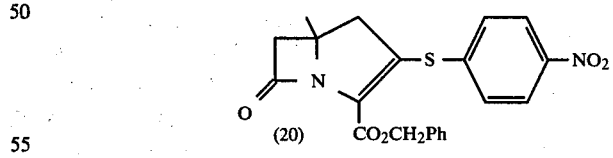
(20)

The phosphorane (35 mg) was refluxed in dry toluene (100 ml) for ten hours. The solvent was evaporated and the product chromatographed on Florisil (200–300 U.S. mesh) to yield the title product as a light yellow crystalline solid from ether mp. 141°–3° (12.5 mg, 61%) $\nu_{max}$ (CHCl$_3$) 1785, 1710, 1525, 1345 cm$^{-1}$. δ ppm (CDCl$_3$) 1.48 (3H, s, CH$_3$), 2.26 (1H, d, J 18 Hz, C6-Ha), 2.93 (1H, d, J 18 Hz, C$_6$-Hb), 5.30 (2H, ABq, J 15 Hz, CH$_2$Ph), 7.30 (5H, m, CH$_2$Ph), 7.85 (4H, ABq, J 9 Hz SPhNO$_2$). No molecular ion but fragment at 368.0844 is correct for M$^+$-[CH$_2$=C=O]C$_{19}$H$_{16}$N$_2$O$_4$S requires 368.0831.

The concentrations of this compound required to inhibit growth of the following bacteria are given below.

| Organism | |
|---|---|
| S. aureus 1517 | 100 |
| Strep. pneumoniae | 20 |
| Strep. pyogenes CN10 | <2 |

EXAMPLE 6 p-Nitrobenzyl-3-phenylthio-5-methyl-7-oxo-1-azabicyclo[3,2,0]-hept-2-ene-2-carboxylate

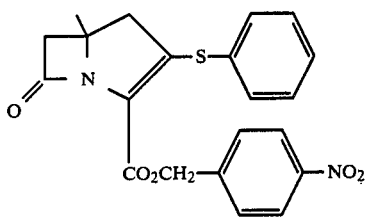

(i) Preparation of 4-methyl-4-phenylthiocarbonylmethyl-azetidin-2-one

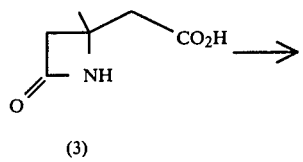

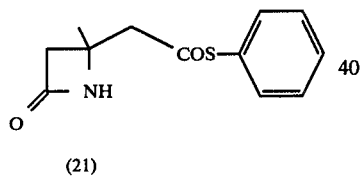

The acid (3) (2.8 g) and triethylamine (2.2 g) in dry T.H.F. (100 ml) were treated with a solution of diethyl phosphorchloridate (3.63) in T.H.F. (25 ml) with stirring at R.T. under argon. Thiophenol (2.2 g) was added, followed by a further equivalent of triethylamine (2.2 g). The reaction was stirred at R.T. for a further two hours, the solvent evaporated and the residue chromatographed. The product (21) was obtained as an oil (2.3 g; 50%) which crystallised from benzene/petrol (60°–80°) as a white microcrystalline solid. m.p. 103°–4° $\nu_{max}$ (CHCl$_3$) 3400, 1760, 1700 cm$^{-1}$. δ ppm (CDCl$_3$) 1.50 (3H, s, CH$_3$), 2.90 (4H, two overlapping quartets coupled to the NH, CH$_2$'s), 6.35 (1H, br.m. NH [exchangeable], 7.35 (5H, s, Ph). (Found: C 61.35; H, 5.65; N, 5.82%. C$_{12}$H$_{13}$NO$_2$S requires C, 61.28; H, 5.53; N, 5.96%).

(ii) Preparation of N-(1-hydroxy-1-p-nitrobenzyloxycarbonylmethyl)-4-methyl-4-phenylthiocarbonylmethyl-azetidin-2-one

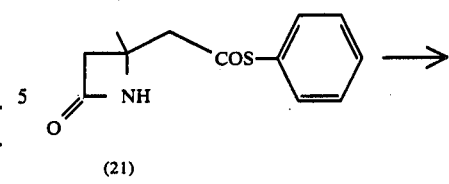

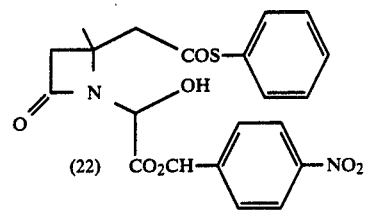

p-Nitrobenzylglyoxylate (4.5 g) was dissolved in benzene (100 ml) and water removed (by azeotroping for one hour). The thioester (21) (2.07 g) was added and the reaction refluxed for a further seven hours. The solvent was evaporated and the residue chromatographed to yield the product (22) contaminated with p-nitrobenzyl glyoxalate. The product was purified by dissolving in ethyl acetate (50 ml), washing with water (2×10 ml), drying and rechromatographing the evaporated organic phase. The product was obtained as an oil (2.2 g; 50%) $\nu_{max}$ (CHCl$_3$) 3,400, 1760(br) cm$^{-1}$. δ ppm (CDCl$_3$) 1.50 and 1.67 (3H, two singlets, CH$_3$ [two isomers]), 2.50 to 3.60 (4H, complex pattern, CH$_2$'s), 4.60 (1H, br.s. OH [exchangeable]), 5.34 (2H, s, benzylic CH$_2$), 5.34 and 5.58 (1H, two singlets, one obscured by the benzylic CH$_2$ and the other sharpening after D$_2$O exchange, CH-OH for two diastereoisomers), 7.44 (5H, s, Ph), 7.54 and 8.25 (4H, ABq, J 9 Hz (iii) Preparation of 1-(1-p-nitrobenzyloxycarbonyl-1-triphenylphosphoranylidene-methyl)-4-methyl-4-phenylthiocarbonylmethyl-azetidin-2-one

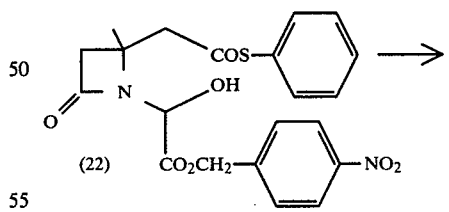

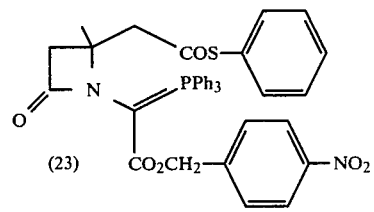

A stirred solution of the carbinol (22) (2.2 g) in T.H.F. (100 ml) was treated with 2,6-lutidine (1.07 g) and thionyl chloride (1.2 g) in T.H.F. (20 ml). Stirring was continued at −20° for 20 minutes. The solution was filtered and azeotroped twice with toluene. The residue was dissolved in dioxan (dried by passage through a basic alumina column) (100 ml) and 2,6-lutidine (1.07 g) and triphenylphosphine (2.62 g) were added. The reaction was stirred at R.T. overnight, the solvent evaporated and the residue chromatographed to yield the thioester phosphorane (23) as an oil (2.2 g; 65%) which crystallised from ethyl acetate as a light yellow microcrystalline solid m.p. 184°–5°. $\nu_{max}$(CHCl$_3$) 1740, 1710, 1605 cm$^{-1}$. (Found: C, 68.11; H, 4.78; N, 4.10%. C$_{39}$H$_{33}$N$_2$O$_6$PS requires C, 68.02; H, 4.80; N, 4.07%).

(iv) Preparation of p-nitrobenzyl-3-phenylthio-5-methyl-7-oxo-1-azabicyclo-[3,2,0]-hept-2-ene-2-carboxylate

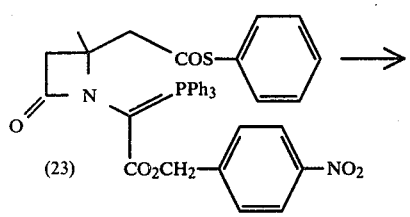

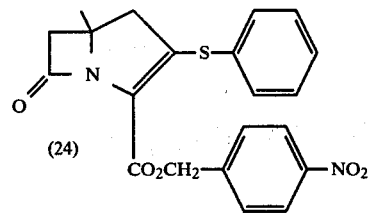

The phosphorane (450 mg) was dissolved in dry toluene (500 ml) and refluxed for 3 days under argon. The solvent was evaporated and the residue chromatographed as florisil (200–300 U.S. mesh) using slight pressure to yield the product (24) as an oil which crystallised from ethyl acetate/petrol (60°–80°) as a light yellow crystalline solid m.p. 142°–6° $\nu_{max}$ (CHCl$_3$), 1780, 1700 cm$^{-1}$. δ ppm (CDCl$_3$) 1.48 (3H, s, CH$_3$), 2.29 (1H, d, J 18 Hz, C6-Ha), 2.95 (1H, d, J 18 Hz, C6-Hb), 5.47 (2H, ABq, J 14 Hz, C$\underline{H}_2$Ph), 7.50 (5H, m, Ph), 8.01 (4H, ABq, J 8 Hz, PhNO$_2$), $\lambda_{max}$(EtOH) 318 nm. (ε 17000), 268 nm (ε 13650). (Found: C, 61.81; H, 4.54; N, 6.75%. C$_{21}$H$_{18}$N$_2$O$_5$S requires C, 61.46; H, 4.39; N, 6.83%).

What we claim is:
1. A compound of the formula (II):

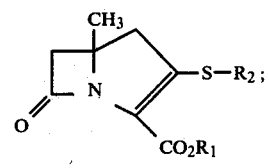

wherein $R_1$ is alkyl of 1 to 4 carbon atoms unsubstituted or substituted by alkoxyl of 1 to 4 carbon atoms or benzyl unsubstituted or substituted by alkoxyl of 1 to 4 carbon atoms, nitro or chloro and $R_2$ is a hydrocarbon of up to 7 carbon atoms unsubstituted or substituted by a CN, NO$_2$, OR$_3$, NH.CO.R$_3$ or CO$_2$R$_3$ group wherein $R_3$ is alkyl of 1 to 4 carbon atoms.

2. A compound according to claim 1 wherein $R_2$ is ethyl.

3. A compound according to claim 1 wherein $R_2$ is 2-acetamidoethyl.

4. A compound according to claim 1 wherein $R_2$ is methoxycarbonylmethyl.

5. A compound according to claim 1 wherein $R_2$ is phenyl.

6. A compound according to claim 1 wherein $R_2$ is t-butyl.

7. The compound according to claim 1 which is t-[B]butyl 3-ethylthio-5-methyl-7-oxo-1-azabicyclo[3,2,0]hept-2-ene-2-carboxylate.

8. A pharmaceutical composition which comprises an antibacterially effective amount of a compound according to claim 1 in combination with a pharmaceutically aceptable carrier.

9. The compound according to claim 1 which is t-butyl-3-(2-acetamidoethyl)thio-5-methyl-7-oxo-1-azabicyclo[3,2,0]-hept-2-ene-2-carboxylate.

10. The compound according to claim 1 which is t-butyl-3-(2-methoxycarbonylmethyl)thio-5-methyl-7-oxo-1-azabicyclo[3,2,0]hept-2-ene-2-carboxylate.

11. The compound according to claim 1 which is t-butyl-3-p-nitrophenylthio-5-methyl-7-oxo-1-azabicyclo[3,2,0]-hept-2-ene-2-carboxylate.

12. The compound according to claim 1 which is benzyl-3-p-nitrophenylthio-5-methyl-7-oxo-1-azabicyclo[3,2,0]-hept-2-ene-2-carboxylate.

13. The compound according to claim 1 which is p-nitrobenzyl-3-phenylthio-5-methyl-7-oxo-1-azabicyclo[3,2,0]-hept-2-ene-2-carboxylate.

* * * * *